United States Patent [19]

Li et al.

[11] Patent Number: 5,001,120
[45] Date of Patent: Mar. 19, 1991

[54] USE OF A-NOR-STEROIDS AS MALIGNANT CELLS GROWTH INHIBITORS

[75] Inventors: Rui-Lin Li, Shanghai, China; David Y. Lee; Qi-Lu Cheng, both of Chapel Hill, N.C.

[73] Assignee: Natural Pharmacia International, Inc., Research Triangle Park, N.C.

[21] Appl. No.: 349,774

[22] Filed: May 10, 1989

[51] Int. Cl.$^5$ .................... A61K 31/56; C07J 61/00
[52] U.S. Cl. .................... 514/548; 514/729; 560/194; 568/817
[58] Field of Search .................... 260/397.5, 169; 514/172, 178, 182; 540/94

[56] References Cited

U.S. PATENT DOCUMENTS 4,898,694  2/1990  Schwartz et al. ............... 260/397.5

FOREIGN PATENT DOCUMENTS 2344749   8/1973   Fed. Rep. of Germany ...... 514/182
3144049  11/1981   Fed. Rep. of Germany ...... 514/182
56-11070  2/1980   Japan .............................. 514/182

OTHER PUBLICATIONS

Pincus et al., "Steroidal Inhibitors of a Cell-Division-Inducing System In Vitro", Steroids 5 (Supl. I), pp. 193–197, (1965).

*Primary Examiner*—Merrell C. Cashion, Jr.
*Assistant Examiner*—C. Azpuru

[57] ABSTRACT

A-Nor-5α-androstane compounds, such as the dipropionate and disuccinate esters of 2α,17α-diethynyl-A-Nor-5α-androstane-2β,17β-diol and the corresponding 2α,17α-diol stereoisomers have an inhibitory effect on malignant cell growth and can be used to treat various carcinomas in mammals.

15 Claims, No Drawings

USE OF A-NOR-STEROIDS AS MALIGNANT CELLS GROWTH INHIBITORS

FIELD OF INVENTION

This invention relates to the use of certain A-nor-steroids as malignant cell growth inhibitors.

BACKGROUND OF THE INVENTION

In the early 1960's (Banik, U.K., Pincus, G., and Jacques, J., 1962, 1964), first reported the implantation inhibition activities exhibited by certain A-nor-steroids as potent progesterone antagonists. In 1965, Pincus and Gordon (1965) reported that A-nor-5α-androstane derivatives, such as 2α,17α-diethyl,2β-17β-diol, 2α-ethynyl-2β, 17β-diol-17α-methyl, 2α-acetyl-17α-ethynyl-17β-ol and 2α-ethynyl-2β,17β-diol, possess antiestrogenic activity, as evidenced by their inhibition of estrogen-induced cell division in amitotic cells of cultured hamster's ascites tumor. However, neither direct evidence nor implication of anti-cancer activity was reported.

In the past two decades, A-nor-steroids have been developed exclusively as anti-fertility agents. See Li, R.L., 1986; Crabbe, P. et al., 1979; and Zhang, Y., 1987. Of the various A-nor-steroids, 2α,17α-diethynyl-A-nor-5α-androstane-2β,17β-diol dipropionate (Anordrin) possesses significant anti-implantation activity in experimental animals (Ku, C.P. et al., 1975), and in clinical trials (Hu, C. et al., 1982). In clinical studies, hyperestrogenic side effect has been noted (Ku, C.P. et al., 1975). Since estrogen is known to cause certain hormonal-dependent cancers, efforts have been made to separate the estrogenic activity from its anti-fertility activity by chemical modifications based on the structure of A-nor-5α-androstane. See Crabbe, P. et al., 1979, Li, R., 1982, and Li, Y.S., 1983, supra. In spite of these extensive activities centered around improving anti-fertility, up to now it has not been recognized that A-nor-5α-androstanes, such as 2α,17α-diethynyl-A-nor-5α-androstane-2β,17β-diol disuccinate and its analogs inhibit malignant cells growth.

OBJECTS OF THE INVENTION

An object of the present invention is to provide A-nor-5α-androstane compositions which are capable of inhibiting malignant cells growth. Another object is to provide a method of inhibiting cell growth in vitro and in vivo. Another object is to provide compositions and methods for the treatment of various cancers. These and other objects of the present invention will be apparent to those skilled in the art to which this invention pertains.

SUMMARY OF THE INVENTION

In a method aspect, this invention relates to a method of inhibiting the growth of malignant cells, which comprises exposing the cells to a cell growth inhibiting amount of a compound of the formula

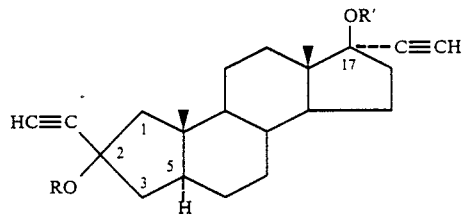

wherein R and R', which can be alike or different, are hydrogen, succinoyl or glutaryl (in free acid or salt form) or propionyl.

In another method aspect, this invention relates to the use of a compound of Formula I for the treatment of carcinomas in mammals.

In a composition aspect, this invention relates to pharmaceutical compositions adapted for the treatment of carcinomas in mammals which comprise a malignant cell growth inhibiting amount of a compound of Formula I.

DETAILED DISCLOSURE

The compounds defined by Formula I are:

- I(a)  2α,17α-diethynyl-A-nor-5α-androstane-2β,17β-diol;
- I(b)  2β,17α-diethynyl-A-nor-5α-androstane-2α,17β-diol.
- I(c)  2α,17α-diethynyl-A-nor-5α-androstane-2β,17β-diol dipropionate (NPI-007, Anordrin, AC-7619);
- I(d)  2α,17α-diethynyl-A-nor-5α-androstane-2β,17β-diol disuccinate (NPI-008) and salts thereof with a base, e.g., sodium and potassium salts;
- I(e)  2β,17α-diethynyl-A-nor-5α-androstane-2α,17β-diol dipropionate (NPI-009);
- I(f) 2β,17α-diethynyl-A-nor-5α-androstane-2α,17β-diol disuccinate (NPI-010) and salts thereof with a base, e.g., sodium and potassium salts;
- I(g)  2α,17α-diethynyl-A-nor-5α-androstane-2β,17β-diol diglutarate and salts thereof with a base, e.g., sodium and potassium salts;
- I(h)  2β,17α-diethynyl-A-nor-5α-androstane-2α,17β-diol diglutarate and salts thereof with a base, e.g., sodium and potassium salts; and
- I(i) the mono and mixed esters corresponding to each of the above diesters.

The A-nor-5α-androstanes of Formula I have the ability to inhibit malignant cell growth, both in vitro and in vivo. Compositions based on these compounds have potent anti-cancer activity in tumor-bearing mammals, e.g., against small cell lung, testicular, esophageal, peptic, colon, breast, endometrial, central nervous system, liver, and prostate cancers and against systemic cancer, e.g., lymphoma and leukemia. In a preferred aspect of this invention, one of these compounds is employed to treat lung, ileocecal, breast or endometrial carcinoma, preferably by administration systemically to a human being suffering therefrom, e.g., orally.

Considerable experimental and clinical evidence exists which indicate that the A-nor-steroids, such as 2α,17α-diethynyl,A-nor-5α-androstane-2β-17β-diol-dipropionate ("Anordrin") possess significant anti-fertility activity. However, no one has reported the anti-cancer activity thereof. This invention establishes for the first time that 2,17α-diethynyl-A-nor-5α-androstane-2,17β-diols whose hydroxy groups are esterified by succinate groups (NPI-008 and -010) or propionate groups (NPI- 007 and -009) possess potent malignant cell growth inhibitory activity. The compounds employed in the present invention differs markedly structurally from existing anti-cancer drugs. They thus lack some of the toxic side effects of the currently known anti-cancer chemotherapeutic agents.

One important use for the compounds and compositions employed in the present invention lies in their ability to inhibit growth of hormone-dependent tumors, such as kidney, breast, endometrial, ovarian, and prostate carcinomas, which are characterized by possessing estrogen or progesterone receptors and which may, therefore, respond to treatment in accordance with the present invention as a consequence of the anti-estrogenic or anti-gestagen activity of the compounds of Formula I wherein OR is an alpha group. However, the compounds of Formula I wherein OR is a beta group lack estrogenic-like activity but nevertheless possess significant malignant cell growth inhibiting activity. Therefore, this activity apparently cannot be attributed solely to anti-estrogenic activity.

Also included within the scope of the present invention are pharmaceutically acceptable salts of salt-forming compounds falling within the scope of the above description. Thus, for example, pharmaceutically acceptable metal, e.g., sodium and potassium, amine, e.g., triethanol-amine and N-methyl-glucamine, and ammonium salts of the succinate and glutarate esters can be employed and the pharmaceutically acceptable acid addition salts, e.g., hydrochloride, sulfate, phosphate, or other inorganic or organic acid, e.g., succinate, glutarate, of the amino-amido-succinoyl and -glutaryl esters, can also be employed.

The present invention is also directed to pro-drug precursors of the active compounds disclosed herein. Such compounds are analogs of the present invention which have favorable physical properties, such as water solubility, for absorption, distribution, or better targeting to the tumor cell. These analogous pro-drug compounds can be produced from the active compounds based on procedures and factors which are well known to those or ordinary skill in the art. Such pro-drug are transformed in vivo to the pharmacologically active drug, e.g., the 2,17$\beta$-diol free alcohol.

Specific cancers which may be mentioned as susceptible to treatment by administration of compounds in accordance with the present invention include endometrial cancer, breast cancer, ovarian cancer, prostate cancer, ileocecal cancer, small cell lung cancer, liver cancer, kidney cancer, and stomach cancer.

The compounds of the present invention can be administered by oral, parenteral, or intravenous routes, or by absorption through the skin or a mucous membrane surface using methods known to those skilled in the art of drug delivery.

For the purpose of therapeutic administration, the active ingredient can be incorporated into a solution or suspension.

Compounds of the present invention can also be administered in combination with other therapeutic anti-cancer treatments, such as radiation therapy, or in combination with other anti-cancer drugs. It is to be understood that dosages may be administered all at once, or may be divided into a number of smaller dosages to be administered at varying intervals of time.

The compounds employed in this invention possess valuable malignant cell growth inhibitor activity. Thus, these compounds can be used for the palliative treatment of a wide variety of solid and systemic carcinomas. They are particularly suited for such use because of the very low toxicity compared to the conventional chemotherapeutic agents. The compounds employed in this invention are generally administered to mammals, including but not limited to humans.

The pharmacologically active compounds of Formula I can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral or enteral, e.g., oral, application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilizates obtained, for example, for the preparation of products for injection.

Oral administration is preferred.

Generally, the compounds employed in this invention are dispensed in unit dosage form, e.g., comprising 0.1 mg to 1.0 g thereof in a pharmaceutically acceptable carrier per unit dosage.

The dosage of the compounds according to this invention generally is 0.1 mg to 1.0 g, preferably 0.5 to 10 mg/kg/day, when administered to patients, e.g., humans, analogous to the known agent tamoxifen or nafoxidine.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate conventional pharmacological protocol.

Contemplated equivalents of the methods of this invention are those employing structurally related A-norsteroids having comparable malignant cell growth inhibiting activity, e.g., compounds of one of the Formulae II and III:

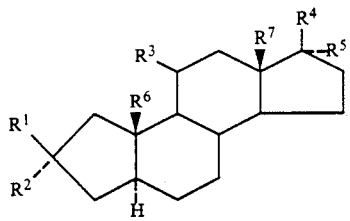

II

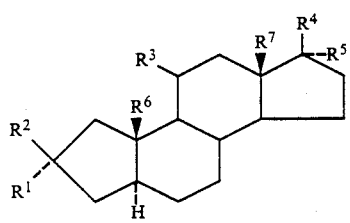

III wherein
R$^1$ is —SH, —NH$_2$, an ester group other than glutaryl, propionyl or succinoyl, preferably one which increases lypophylicity, e.g., in the case of compounds intended for injection, or hydrophilicity, e.g., in the case of compounds intended for oral administration, and/or resistance to enzymatic cleavage, e.g.,

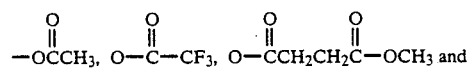

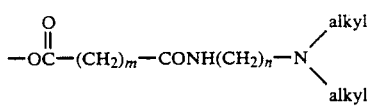

wherein m and n are integers from 1 to 4, preferably m is 2 or 3 and n is 3, and alkyl is of 1 to 4 carbon atoms, preferably 1, and acid addition salts thereof, e.g., HCl, a carbamide group, e.g., —NHCOC$_2$H$_5$ and —NHYCOCH$_2$CH$_2$COOH, or an acyl group, e.g.,

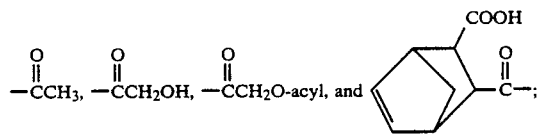

R$^2$ is —C≡CH, —C≡C—CH$_3$, or —CH$_2$CN;
R$^3$ is —H or substituted phenyl, preferably in the p-position, e.g.,

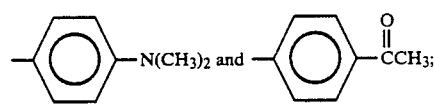

R$^4$ is as defined above for R$^1$
R$^5$ is —H, —C≡CH, —C≡C—CH$_3$, OR —CH$_2$CN;
R$^6$ is CH$_3$ or H; and
R$^7$ is CH$_3$ or C$_2$H$_5$;

and compounds otherwise corresponding to one of Formulae II and III wherein R$^1$ and R$^4$ are —OH or an ester group as defined above for Formula I and R$^2$ and/or R$^5$ is other than —C≡CH or R$^3$ and/or R$^6$ is other than H, or R$^7$ is —C$_2$H$_5$, including (a) those wherein R$^1$ and R$^4$ are ester groups, e.g., succinyloxy, β-carboalkoxypropionyloxy and propionyloxy, (b) those wherein R$^4$ is OH or an acyl group, e.g.,

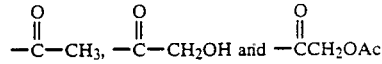

(c) those of Formula II wherein

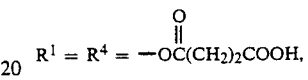

wherein m is 2 or 3, or

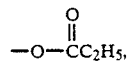

R$^2$=R$^5$=—C≡CH or —C≡C—CH$_3$ and R$^3$ is H,
(d) those of Formula III wherein

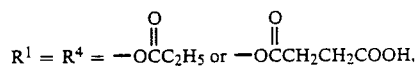

R$^2$=R$^5$=—C≡CH or —C≡C—CH$_3$ and R$^3$ is H,
(e) those wherein R$^2$=R$^5$= —C≡CH or —C≡C—CH$_3$, R$^1$=R$^4$= OH and R$^3$ is H, especially those of Formula II,
(f) those wherein R$^6$ is H, and
(g) those wherein R$^3$ is

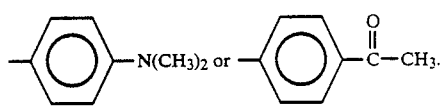

Standard procedures, such as esterification, hydrolysis, amidation of carboxylic acids or esters, lead to the substituents R$^1$, R$^2$, R$^4$, and R$^5$.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, unless otherwise indicated, all parts and percentages are by weight.

The entire texts of all applications, patents, and publications, if any, cited above and below, are hereby incorporated by reference.

EXAMPLE 1

Synthesis of 2α,17α-Diethynyl-A-nor-5α-androstane-2β,17β-diol-disuccinate (NPI-008)

Epidehydro-androstane acetate (50 g) was dissolved in ethanol (1.0 l) and treated with pd/CaCO$_3$ (12.5 g) under H$_2$ (1 atm) at 25° C. The catalyst was filtered and the filtrate was diluted with NaOH solution (12 g/24 ml water) and refluxed for 30 min. Excess ethanol was distilled off and the resulting solution (200 ml) was diluted with water. The precipitates was collected and washed to provide 43.4 g (99% yield) of hydrolyzed product, 5α-androstane-2β-ol-17-one, mp 172.5°–173.5° C. (recrystallized from E to H) (lit. 175°–176° C.). Anal. Calcd. for C$_{19}$H$_{10}$O$_2$: C, 78.57; H, 10.41. Found: c, 78.58; H, 10.65.

The hydrolyzed product (30 g) in glacial acetic acid (300 ml) was warmed to 55°–60° C. and was added slowly to a mixture consisting of chromic acid (35 g), ice-water (240 g) and concentrate sulfuric acid (48 ml) within 1½ hour. The reaction mixture was warmed to 90° C. for 30 min. and acetic acid was distilled. The residue was treated with NaOH solution followed by filtration. The filtrate was reacidified and the precipitate was filtered and washed to give the A-ring diacid (27 g, 77.2% yield); mp 231°–233° C. (lit. 228°–232° C.). Anal. Calcd. for C$_{19}$H$_{28}$O$_5$: C, 67.83; H, 8.39. Found: C, 68.18; H, 8.33.

Under alkali conditions, the thus-produced A-ring diacid 17-ketone (20 g) was reduced with KBH$_4$ (3.5 g) at 80° C. to provide the corresponding 17β-ol compound; m.p. 278°–280° C. (recrystallized from EtOAc/MeOH). To 10 g of this, diacid in acetic anhydride (50 ml) was added sodium acetate (2 g) and the mixture was refluxed for 4 hours. The solvent was distilled under 150° C. and the residue was cooled, treated with ethanol and neutralized to pH 9 with NaOH solution. Ethanol was removed under reduced pressure, the product was precipitated to give the ring closed 2-ketone, A-nor-5α-androstane-17β-diol-2-one (6.1 g) mp. 191°–193° C.

A mixture of KOH (15 g), THF (30 ml) and acetone (0.5 ml) was cooled to 5° C. and saturated with acetylene gas. The thus-produced 2-keto compound (10 g) dissolved in 10 ml THF was added thereto at 5° C. The reaction was complete in 1 hour and the product was diluted with water, acidified and extracted to give 9.85 g of 2α-ethynyl-A-nor-5α-androstane-2β,17β-diol; mp=178° C., [α]$_D$ +23.6°. A very small amount of 2β-ethynyl isomer was also isolated; mp: 210° C. [α]$_D$ −4°. If the above ethynylation is kept at 40° C., the 2β-ethynyl isomer becomes the major product with an α:β ratio of 4:6. Ethynylation of the C-17 keto group following the above reaction conditions at 5° C. provided 2α,17α-diethynyl-A-nor-5α-androstane-2β,17β-diol; mp. 166°–167° C., [α]$_D$ −64°.

Esterification with appropriate anhydride in dry pyridine gave the desired 2β,17β-disuccinate ester (NPI-008); mp. 220°–224° C. [α]$_D$ −24.6°; ′HNMR δ2.56 and 2.54 (2S, C≡CH), 2.55 (bs O-CH$_2$CH$_2$-8H), 0.86 (19-CH$_3$), 0.83 (18-CH$_3$). For 2β,17β-dipropionate (NPI-007); mp: 152°–153° C., [α]$_D$ −32° C.; ′HNMR 2.56 and 2.53 (2s C≡CH), 1.13 (t, 2xCH$_2$CH$_3$ J=8 Hz), 0.86 (19-Me), 0.83 (18-CH$_3$); Ms: m/e 438.

Similarly, esterification stepwise, e.g., with succinic and propionic anhydrides produces a mixture of the diesters, e.g., 2β-propionate,17β-succinate and 2β-succinate,17β-propionate esters, which can be isolated in a conventional manner by column chromatography.

The corresponding diesters of 2β,17α-ethinyl-A-nor-androstane-2α,17β-diol are similarly prepared.

The following A-nor steroids corresponding to Formula I were produced according to the procedure of Example 1:

| Product | | Anhydride Reagant |
|---|---|---|
| | 2β, 17β-Diesters | |
| 1 | R: —C(=O)CH$_3$ (diacetate) <br> mp: 190–191° C. <br> [α]$_D$ −39° | Ac$_2$O/p.t.s. |
| 2 | R: —C(=O)C$_2$H$_5$ (dipropionate) <br> mp: 152–153° C. <br> [α]$_D$ −32° | Pr$_2$O/p.t.s. |
| 3 | R: —C(=O)C$_3$H$_7$ (dibutyrate) <br> mp: 145–147° C. | Bu$_2$O/p.t.s. |
| 4 | R: —C(=O)CH$_2$CH$_2$COOH (disuccinate) <br> mp: 220–224° C. <br> [α]$_D$ −24.6° | succinic anhydride/pyr. |
| 5 | R: —C(=O)CH$_2$CH$_2$COOCH$_3$ <br> mp: 288–90° C. | CH$_3$OOCCH$_2$CH$_2$C(=O)—O—C(=O)CH$_2$CH$_2$OOCH$_3$ /p.t.s. |
| | 2α, 17β-Diester | |
| 6 | R: —C(=O)C$_2$H$_5$ (dipropionate) | Pr$_2$O/p.t.s. |

A = acetyl, Pr = propionyl, Bu = butyryl, p.t.s. = p-toluenesulfonic acid, pyr.-pyridine.

EXAMPLE 2

In vitro Studies of NPI-007 and NPI-008 Against Various Tumor Cells

The procedure of Geran, R. T., et al. Cancer Chemother. Rep. (Part 3) 3,1 (1972) (see K. H. Lee et al., Planta Medica, 308, 1988), was employed to determine the in vitro ED$_{50}$ dose for NPI-007 and NPI-008 against human tumor cells, including the lymphoid leukemia (L 1210), the lung carcinoma (A-549), the ileocecal carcinoma (HCT-8), and the mammary gland carcinoma (MCF-7) cell lines. These cell lines were obtained from the American Type Culture Collection (Rockville, Md.).

TABLE I

| | ED$_{50}$ (μg/ml) (N = 4) Tumor Cells | | | |
|---|---|---|---|---|
| Compound | L 1210 | A-549 | HCT-8 | MCF-7 |
| NPI-007 | 4.50 | >10 | 0.57 | 5.9 |
| NPI-008 | 5.87 | >10 | 0.41 | 7.6 |
| Vinblastine sulfate | — | 0.003 | 0.005 | — |
| Adriamycin HCl | — | 0.16 | 0.3 | — |

TABLE I-continued

| Compound | ED$_{50}$ ($\mu$g/ml) (N = 4) Tumor Cells | | | |
|---|---|---|---|---|
| | L 1210 | A-549 | HCT-8 | MCF-7 |
| etoposide | 1.58 | — | — | — |

EXAMPLE 3

In vivo Anti-Cancer Activity

Material and Methods:

Swiss albino female mice of 10–12 weeks old, weighing 17–20 grams were separated into two groups.

Sarcoma-180, Ehrlich ascite tumor (ECA) and U$_{14}$ cell lines were separately maintained and propagated in MEM-F12 medium supplemented with 10% FCS. The cells were detached to suspension by use of 0.25% trypsin solution. After suspension, the cells were washed once with PBS and resuspended in sample buffered solution. The cells were counted by a coulter particle counting apparatus. Cells sized from 10–100 $\mu$ were obtained for calculation of dosage.

Animals were restrained manually and 0.2 ml cell suspension containing $10^7$ to $2 \times 10^7$ cells/ml for S180, U$_{14}$ or ECA were injected subcutaneously in left thorax ventrally adjacent to axillae. The selected A-nor-5$\alpha$-androstane (5 mg) was dissolved in 2.5 ml phosphate buffered saline (pH 7.4) solution. A solution (0.1 mg/0.05 ml) was injected into thigh muscle every other day for 5 consecutive treatments. The injection site was alternated between right and left legs. No untoward signs were observed in all mice injected. Control animals received injection of the same amount of PBS in a manner similar to the treated groups.

At 2 days after the last (5th) treatment, animals were sacrificed by suffocation with carbon dioxide gas. The skin over the tumor site was reflected and the tumor mass dissected free from connective tissue and weighted with an electric balance.

The results are shown in Table II.

TABLE II

| | | In vivo Tumor Growth Inhibition Assay | | |
|---|---|---|---|---|
| Tumor Cell Lines | Testing Compounds | Treatment Group Wet Weight of Tumor (g $\times$ $\pm$SE) | Control Group Wet Weight of Tumor (g $\times$ $\pm$SE) | Inhibition % |
| ECA | NPI-007 | 0.1957 $\pm$ 0.0165 (5) | 0.4162 $\pm$ 0.0767 (5) | 52.9 |
| | NPI-008 | 0.0416 $\pm$ 0.0120 (5) | 0.4162 $\pm$ 0.0767 (5) | 90.0 |
| M$_{14}$ | NPI-007 | 0.6464 $\pm$ 0.0536 (5) | 1.1413 $\pm$ 0.1225 (5) | 43.4 |
| | NPI-008 | 0.2785 $\pm$ 0.0308 (5) | 1.1413 $\pm$ 0.1225 (5) | 75.6 |
| S$_{180}$ | NPI-007 | 0.5428 $\pm$ 0.1059 (5) | 2.0939 $\pm$ 0.3835 (5) | 74.1 |
| | NPI-008 | 0.2722 $\pm$ 0.0872 (5) | 2.0939 $\pm$ 0.3835 (5) | 87.0 |

TABLE III

| | In vivo Antitumor Activity Against Lewis Lung Carcinoma in Mice (DBF$_1$) | | |
|---|---|---|---|
| | Treatment (Dosage) | Tumor Weight (mg) | |
| | mg $\times$ 7 Days | 3 Days After Treatment | 8 Days After Treatment |
| Control | 0 | 310 $\pm$ 51.5 (10)+ | 772 $\pm$ 360 (11) |
| NPI-008 | 0.1 | 168 $\pm$ 53 (10) | 175 $\pm$ 153 (11) |
| Cyclophosphamide* | 0.4 | 130 $\pm$ 31 (10) | 500 $\pm$ 275 (11) |

*Cyclophosphamide is the most commonly used chemotherapeutic agent in the treatment of cancer in humans.
+Number of mice The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

REFERENCES

Banik, U.K., and Pincus, G. 1962. Proc. Soc. Exp. Biol. Med. 111:595.

Crabbe, P. et al. 1979. Chemical synthesis and bioassay of anordrin and dinordrin I and II. Steroids, Vol. 33, No. 1, p. 85.

Gevan, R. T., Greenberg, M. M., MacDonald, A. M., Schumacher, A. M., Abbott, B. J., Cancer Chemother. Rep. (Part III) 3.1 (1972).

Gu, Z. et al. 1979. A-Nor-steroids as post-coital contraceptives in the hamster with special reference to the transport and degeneration of eggs. Contraception, Vol. 20, No. 6, p. 549.

Gu, Z. et al. 1984. Studies on the antifertility effects of anordrin and its analogs. Shengli Xuebao, Vol. 36, No. 6, p. 611.

Gu, Z. et al. 1986. The antifertility effect of anordrin and AF-45. Shengzhi Yu Biyun, Vol 6, No. 2, p. 14.

Hu, C. Y. et al. 1982. In: Endometrial bleeding and steroidal contraception. WHO Symposium, Geneva, pp. 191–200.

Jacques, J. and Pincus, G., Proc. 1st Cong. on Hormonal Steroids Excerpta. Medica Press, Amsterdam, 1962, p. 3.

Ku, C. P. et al. 1975. Scientia Sinica. 18:262.

Lee, K. H. et al., planta Medica. 308 (1988).

Li, R. L. et al. 1986. Synthesis and anti-fertility activities of A-Nor-steroidal compounds. Yiyao Gongye, Vol. 17, No. 9, pp. 404–13.

Li, S. 1986. Antifertility activity of anordrin analogs. Huaxi Yike Daxue Xuebao, Vol. 17, No. 1, p. 48.

Li, S. et al. 1986. Effects of anordrin on the development of implantation site in mice. Shengzhi Yu Biyun, Vol. 6, No. 4, 31.

Liu, C. Q. et al. 1985. Effects of anordrin and its analogs on antifertility. Contraception, Vol. 32, No. 3, p. 301.

Mehta, R. R. et al. 1982. Antagonism of the actions of estrogens, androgens and progesterone by anordrin. Steroids, Vol. 40, No. 1, p. 65.

Mehta, R. R. et al. 1981. Antiestrogenic and antifertility actions of anordrin. Steroids, Vol. 38, No. 6, p. 679.

Pincus, G., Banik U.K. and Jacques, J., 1964. Steroids 4, 657.

Pincus, G., and Gordon, H. 1965. Steroidal inhibitors of a cell-division-inducing system in vitro. Steroids 5 (Supl. I), p. 193.

Zhang, Y. et al. 1987. Effect of anordrin on egg transport and in vitro fertilization of mouse. Shengzhi Yu Biyun, Vol. 7, No. 2, p. 63.

What is claimed is:

1. A method of inhibiting the growth of malignant cells, which comprises contacting the tumor cells in vitro, or administering in vivo to a tumor bearing mammal, a cell growth inhibiting amount of a compound of the formula

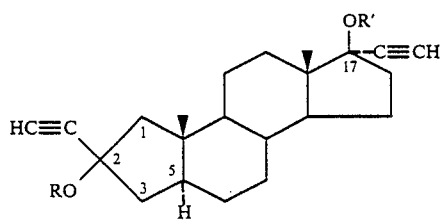

wherein R and R' are H, succinoyl or glutaryl in free acid or salt of a pharmaceutically acceptable salt of a base form, or propionyl.

2. The method according to claim 1, wherein the OR group is in the alpha stereoconfiguration.

3. The method according to claim 1, wherein the compound is $2\beta,17\alpha$-diethynyl-A-nor-$5\alpha$-androstane-$2\alpha,17\beta$-diol disuccinate or diglutarate or the corresponding disodium, dipotassium or triethanolamine salt thereof.

4. The method according to claim 1, wherein the compound is $2\beta,17\alpha$-diethynyl-A-nor-$5\alpha$-androstane-$2\alpha,17\beta$-diol dipropionate.

5. The method according to claim 1, wherein the OR group is in the beta stereoconfiguration.

6. The method according to claim 1, wherein the compound is $2\alpha,17\alpha$-diethynyl-A-nor-$5\alpha$-androstane-$2\beta,17\beta$-diol disuccinate or diglutarate or the corresponding disodium, dipotassium or triethanolamine salt thereof.

7. The method according to claim 1, wherein the compound is $2\alpha,17\alpha$-diethynyl-A-nor-$5\alpha$-androstane-$2\beta,17\beta$-diol dipropionate.

8. The method of claim 1, wherein the malignant cells are present in a mammal and the compound is administered systematically thereto.

9. The method of claim 8, wherein the mammal is a human being.

10. The method of claim 9, wherein the compound is administered orally.

11. The method of claim 9, wherein the malignant cells are lung, ileocecal, breast or endometrial carcinoma cells.

12. The method according to claim 9, wherein the compound is $2\beta,17\alpha$-diethynyl-A-nor-$5\alpha$-androstane-$2\alpha,17\beta$-diol disuccinate.

13. The method according to claim 9, wherein the compound is $2\beta,17\alpha$-diethynyl-A-nor-$5\alpha$-androstane-$2\alpha,17\beta$-diol dipropionate.

14. The method according to claim 9, wherein the compound is $2\alpha,17\alpha$-diethynyl-A-nor-$5\alpha$-androstane-$2\beta,17\beta$-diol disuccinate.

15. The method according to claim 9, wherein the compound is $2\alpha,17\alpha$-diethynyl-A-nor-$5\alpha$-androstane-$2\beta,17\beta$-diol dipropionate.

* * * * *